(12) United States Patent
Ju et al.

(10) Patent No.: US 9,891,178 B2
(45) Date of Patent: Feb. 13, 2018

(54) INDUSTRIAL CT SCANNING TEST SYSTEM

(71) Applicant: CHINA UNIVERSITY OF MINING AND TECHNOLOGY, BEIJING, Beijing (CN)

(72) Inventors: Yang Ju, Beijing (CN); Jianqiang Wang, Beijing (CN); Ruidong Peng, Beijing (CN); Lingtao Mao, Beijing (CN); Hongbin Liu, Beijing (CN)

(73) Assignee: CHINA UNIVERSITY OF MINING AND TECHNOLOGY, BEIJING, Beijing (CN)

( * ) Notice: Subject to any disclaimer, the term of this patent is extended or adjusted under 35 U.S.C. 154(b) by 0 days.

(21) Appl. No.: 15/539,835

(22) PCT Filed: Jul. 5, 2016

(86) PCT No.: PCT/CN2016/088557
§ 371 (c)(1),
(2) Date: Jun. 26, 2017

(87) PCT Pub. No.: WO2017/012465
PCT Pub. Date: Jan. 26, 2017

(65) Prior Publication Data
US 2017/0350833 A1    Dec. 7, 2017

(30) Foreign Application Priority Data
Jul. 21, 2015  (CN) .......................... 2015 1 0431501

(51) Int. Cl.
*A61B 6/00*         (2006.01)
*G01N 23/00*        (2006.01)
(Continued)

(52) U.S. Cl.
CPC .......... *G01N 23/046* (2013.01); *G06T 11/005* (2013.01); *G06T 2207/10081* (2013.01); *G06T 2211/428* (2013.01)

(58) Field of Classification Search
CPC ...................................................... A61B 6/032
See application file for complete search history.

(56) References Cited

U.S. PATENT DOCUMENTS

| 4,856,341 A | 8/1989 | Vinegar et al. |
| 2008/0013089 A1* | 1/2008 | Ishii ...................... G03F 9/7011 356/400 |

FOREIGN PATENT DOCUMENTS

| CN | 2924518 Y | 7/2007 |
| CN | 102004053 A | 4/2011 |

(Continued)

OTHER PUBLICATIONS

International Search Report for PCT/CN2016/088557, dated Aug. 29, 2016, ISA/CN.
(Continued)

*Primary Examiner* — Dani Fox
(74) *Attorney, Agent, or Firm* — U.S. Fairsky LLP; Yue Xu

(57) ABSTRACT

An industrial CT scanning test system. The test system includes a test base, a multi-axis motion swivel table supported on the test base, a ray generator, an image acquisition device, and a fluid pressure loading device, and further includes a control device. The fluid pressure loading device includes at least one loading cylinder, and in case of performing a scanning experiment, the at least one loading cylinder is placed on a sample stage of the multi-axis motion swivel table together with a sample, and real-time loading of loads in different directions on the sample is performed according to test requirements.

20 Claims, 6 Drawing Sheets

(51) Int. Cl.
    *G01N 23/04*     (2006.01)
    *G06T 11/00*     (2006.01)

(56) References Cited

FOREIGN PATENT DOCUMENTS

| | | |
|---|---|---|
| CN | 102042989 A | 5/2011 |
| CN | 102809574 A | 12/2012 |
| CN | 104101536 A | 10/2014 |
| WO | 2004019029 A1 | 3/2004 |

OTHER PUBLICATIONS

Nie, Baisheng et al.;"Meso-Structures Evolution Rules of Coal Fracture with the Computerized Tomography Scanning Method", Engineering Failure Analysis, vol. 41, Oct. 21, 2013 (Oct. 21, 2013), ISSN: 1350-6307, pp. 81-88.
Mao, Lingtao et al. "Construction and Application of a Mechanics Experimental Platform Based on Industrial Computer Tomography (CT)", CT Theory and Applications, vol. 24, No. 2, Mar. 31, 2015 (Mar. 31, 2015), ISSN:1004-4140, pp. 271-282.

\* cited by examiner

INDUSTRIAL CT SCANNING TEST SYSTEM

This application is the national phase of International Application No. PCT/CN2016/088557, titled "INDUSTRIAL CT SCANNING TEST SYSTEM", filed on Jul. 5, 2016, which claims the benefit of priority to Chinese patent application No. 201510431501.X titled "INDUSTRIAL CT SCANNING TEST SYSTEM" and filed with the Chinese State Intellectual Property Office on Jul. 21, 2015, the entire disclosures of which are incorporated herein by reference.

FIELD

This application relates to the technical field of sample scanning, and particularly to an industrial computed tomography scanning test system.

BACKGROUND

Industrial computed tomography (CT) scanning technique provides an effective laboratory technique for the analysis and study of internal structures of materials and is widely used in various related fields.

A conventional industrial CT generally uses X-rays to penetrate a section of an object, and performs a rotational scan, to reconstruct an image of the internal part of the object by means of a high-performance computer system. The principle is described as follows. The intensity of X-rays after penetrating the object to be detected is measured by a specific detector, and in the meantime, a scanning action among the X-ray machine, the detector and the object to be detected is performed, thus obtaining complete data required for reconstructing a CT image, and finally, the image of the section of the object is reconstructed by using these data based on a certain algorithm.

However, due to essential characteristics of the industrial CT scanning technique, to obtain a better resolution, in one aspect, the size of a focus of the ray beam is required to be reduced as much as possible, to restrict the penetrating ability of the rays; and in another aspect, the size of the sample should be carefully restricted and a stable rotation of the sample during the scanning should be guaranteed, to restrict the dimension of an object to be scanned. These restrictions adversely affect the application of the CT technique in mechanics analysis to a great extent. A loading device is indispensable in mechanics experiments; however, a conventional loading device generally has a large volume and weight, and is hence difficult to be directly placed in the industrial CT machine to be used in the scanning process. Therefore, in the conventional technology, loading is generally performed outside of the CT machine, and then the loaded sample is placed on a test-bed of the CT. This loading method has a low accuracy, and once the loading is finished, the load applied to the test sample is not adjustable.

For homogeneous materials such as metal, rubber, and ceramic, a small sample and a miniature loading device may be used for the scan and analysis, which may ensure that rays are able to penetrate the sample to form an image, and the image can meet the requirement for a certain resolution ratio. However, for the analysis of the mechanical loading performed on a geotechnical material, the following challenges should be overcome. Firstly, the sample cannot be too small; otherwise, the analysis may be influenced by a dimensional effect such that a desired experimental result cannot be obtained. However, the increase in the size of the sample may inevitably result in the increase in the size of the loading device, thus causing a series of issues such as, rays are difficult to penetrate the sample, the loading tonnage is increased, and the resolution ratio of the image is decreased. Secondly, loading schemes are generally complicated; to simulate a stress state of the geotechnical material in practical engineering, a simple uniaxial tensile and compression experiment is not sufficient, various complicated loading experiments are further required, such as multi-axial compression experiment, percolation experiment, and hydraulic fracturing experiment. Also, sometimes loading and unloading procedures are required to be performed many times. Hence, a higher requirement is imposed on the implementation and control of the loading device.

Therefore, a technical issue to be addressed by those skilled in the art is to provide an industrial CT scanning test system, which can realize multi-directional loading on a sample, to meet test requirements.

SUMMARY

An industrial CT scanning test system is provided according to the present application, which can achieve real-time loading of a test sample and improve simulation accuracy of the system, and can achieve multi-directional loading on the sample, to meet test requirements.

In order to address the above technical issues, an industrial CT scanning test system is provided according to the present application, which includes a test base, a multi-axis motion swivel table supported on the test base, a ray generator, an image acquisition device, and a fluid pressure loading device, and further includes a control device;

the multi-axis motion swivel table is provided with a sample stage configured to allow a sample to be placed thereon, and the sample stage is rotatable or movable in a preset direction with respect to the test base according to test requirements;

the ray generator is configured to emit rays required for scanning the sample;

the image acquisition device is arranged in a side opposite to the ray generator, and is configured to acquire the rays emitted by the ray generator and perform imaging of the sample according to the rays acquired;

the fluid pressure loading device includes at least one loading cylinder, and in case of performing a scanning experiment, the at least one loading cylinder is placed on the sample stage of the multi-axis motion swivel table together with the sample, and real-time loading of loads in different directions on the sample is performed according to test requirements; and the control device is configured to control actions of the multi-axis motion swivel table, the ray generator, the image acquisition device, and the fluid pressure loading device.

In the industrial CT scanning test system, the fluid pressure loading device is employed, the self weight of the loading device is reduced as much as possible, and the loading device can provide a large loading force, and the requirements of deformation and destructive tests for most of geotechnical materials may be met. Also, the loading device of the loading device and the sample are placed together on the sample stage of the multi-axis motion swivel table to be scanned by the rays together, and the loading force applied onto the geotechnical sample by the loading cylinder may be adjusted in real time according to test requirements, thus improving the efficiency of the test.

Also, the loading of forces in different directions on the sample may be realized by adjusting the number of loading cylinders. For example, providing two loading cylinders may realize the loading of forces in two directions on the sample. Providing three loading cylinders may realize the loading of forces in three different directions on the sample, for example, a simulation experiment in which forces in three-axis coordinate system are loaded may be performed.

Optionally, the fluid pressure loading device includes a body, and a sample accommodating cavity and at least one fluid medium cavity are provided inside the body, a piston is provided in each of the at least one fluid medium cavity and separates the respective fluid medium cavity into two chambers, including one chamber in communication with an external hydraulic medium via an oil passage provided inside the body, and another chamber in communication with the sample accommodating cavity; and one end, facing the sample accommodating cavity, of each piston is extendable into the sample accommodating cavity; and the fluid medium cavity and the piston constitute the loading cylinder.

Optionally, the fluid medium cavities includes a first fluid medium cavity and a second fluid medium cavity; correspondingly, the pistons includes a first piston and a second piston, the first piston is placed inside the first fluid medium cavity, the second piston is placed inside the second fluid medium cavity, and an axial direction of the first piston and an axial direction of the second piston are arranged to be perpendicular to each other.

Optionally, the fluid medium cavities further includes a third fluid medium cavity, a third piston is provided inside the third fluid medium cavity, and an axial direction of the third piston, the axial direction of the second piston and the axial direction of the first piston constitute a three-axis coordinate system, and one of the fluid medium cavities is vertically arranged.

Optionally, in an axial direction of the piston, a cross sectional dimension of a first end surface of the piston is greater than a cross sectional dimension of a second end surface of the piston, the first end surface is an end surface towards an end of the fluid medium cavity, and the second end surface is an end surface towards an end of the sample accommodating cavity.

Optionally, the body is further provided with an auxiliary hole at a portion opposite to the fluid medium cavity, and the auxiliary hole has a radial dimension smaller than a radial dimension of the fluid medium cavity; and a plug matching with the auxiliary hole is further provided.

Optionally, in a longitudinal cross section of the body, a wall thickness, at a side where the fluid medium cavity is provided, of the body is greater than a wall thickness at the opposite side of the body.

Optionally, the body is further provided with a passage configured to communicate a lower surface of the body with the sample accommodating cavity, to facilitate disposing the sample into the sample accommodating cavity through the passage, and an inlet end of the passage is provided with a plug.

Optionally, oil ports configured to communicate with an external fluid medium source are all arranged in an upper end surface of the body, and the oil ports are in communication with respective fluid medium cavities via internal oil passages.

Optionally, the industrial CT scanning test system further includes two connection heads, wherein an upper end and a lower end of the body are each provided with a flange, and the two connection heads are connected to the flanges at the two ends of the body via bolts.

Optionally, the industrial CT scanning test system further includes a synchronously rotating device, wherein the synchronously rotating device includes a fixed holder and a cantilevered holder, a lower end of the fixed holder is supported on the test base, and an upper end of the fixed holder is vertically rotatably connected to the cantilevered holder;

a guide rail, a slider configured to cooperate with the guide rail to slide, and a driving component configured to drive the slider to move along the guide rail are provided on the cantilevered holder; and a medium pipeline configured to communicate with the loading cylinder is limited in the slider, and extends downward from the slider to connect the loading cylinder located on the sample stage.

Optionally, the cantilevered holder includes two transverse beams extending horizontally, an end plate connected to front ends of the two transverse beams, and a third support plate connected to rear ends of the two transverse beams, the driving component is arranged above the third support plate, and the third support plate is rotatably connected to the fixed holder, and the guide rail is arranged on upper surfaces of the two transverse beams.

Optionally, the synchronously rotating device further includes a multi-passage high pressure rotator fixedly connected to the slider, the multi-passage high pressure rotator includes a fixed-end pipe joint and a rotary-end pipe joint which are in communication with each other via an internal passage, and the fixed-end pipe joint is in communication with a driving source via a pipeline, and the rotary-end pipe joint is in communication with the loading cylinder via a pipeline, and the rotary-end pipe joint is rotatable synchronously with the sample stage.

Optionally, the industrial CT scanning test system further includes a rotatable holder arranged between the fixed holder and the cantilevered holder, wherein, the fixed holder includes an upright column, and a bottom of the upright column is supported on the test base, and an upper end of the upright column is further provided with a horizontal support plate; and the rotatable holder includes a central column, a lower end of the central column is inserted into the upper end of the upright column and is circumferentially rotatably connected to the upper end of the upright column via a bearing, a gear is further fixed onto the central column, and a motor configured to drive the gear to rotate is further provided, and is fixed to the horizontal support plate; and a second supporting plate is fixed to an upper end of the central column, and the cantilevered holder is fixed to the second support plate.

Optionally, the driving component includes a motor, a lead screw, and a nut seat configured to cooperate with a threaded end of the lead screw, the threaded end of the lead screw is arranged in an inner threaded hole of the nut seat, and another end of the lead screw is fixedly connected to the slider, and the motor is configured to drive the lead screw to rotate, to allow the lead screw to drive the slider to reciprocate.

Optionally, the industrial CT scanning test system further includes an automatic winder arranged below the sample stage, wherein the automatic winder includes a threaded rod, a nut assembly and a bobbin, an upper end of the threaded rod is fixedly connected to the sample stage, and a lower end of the threaded rod passes through a threading hole of the sample stage to extend downward; and the nut assembly includes a nut and a limiting component configured to limit the position of the nut with respect to a fixing frame of the multi-axis motion swivel table circumferentially, and the nut has inner screw threads configured to cooperate with an outer threaded portion of the threaded rod;

and the bobbin is sleeved on the threaded rod, the bobbin and the threaded rod are axially movably connected, and the bobbin is fixedly connected to the nut.

Optionally, the limiting component includes guide rods respectively located at two sides of the threaded rod and a sliding plate sleeved on the two guide rods, the sliding plate is axially slidably connected to the guide rods, and the sliding plate is fixedly connected to the nut.

Optionally, the limiting component further includes a connecting plate fixedly connected to tail ends of the two guide rods, a bearing is provided on the connecting plate, and a free end of the threaded rod is connected to the connecting plate via the bearing.

Optionally, the image acquisition device includes a flat panel detector and a movable platform, and the flat panel detector is supported on the movable platform, and the movable platform is movable with respect to the test base in an emitting direction of a principle ray beam.

Optionally, the industrial CT scanning test system further includes a stress-strain acquisition device configured to acquire stress-strain parameters of the sample in various directions; wherein the control device is configured to control a pressure of a fluid medium in the fluid pressure loading device according to the stress-strain parameters.

BRIEF DESCRIPTION OF THE DRAWINGS

For more clearly illustrating embodiments of the present application or the technical solutions in the conventional technology, drawings referred to describe the embodiments or the conventional technology will be briefly described hereinafter. Apparently, the drawings in the following description are only some examples of the present application, and for the person skilled in the art, other drawings may be obtained based on these drawings without any creative efforts.

Figure 1:
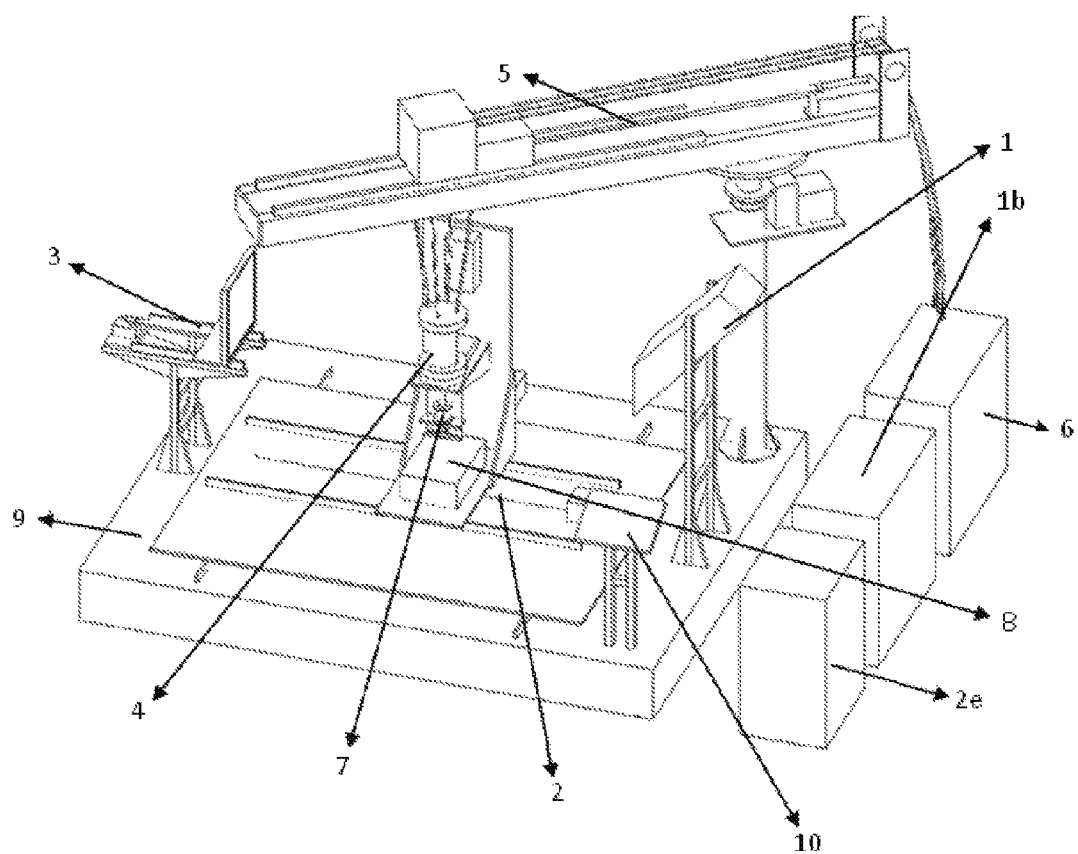
FIG. 1 is a schematic view showing the structure of an industrial CT scanning test system according to an embodiment of the present application.

Corresponding relationships between names of components in FIGS. 1 to 8 and reference numerals are as follows:

| 1 | ray generator, | 1b | high pressure generator, |
|---|---|---|---|
| 2 | multi-axis motion swivel table, | 2e | control cabinet, |
| 3 | image acquisition device, | 4 | fluid pressure loading device, |
| 41 | body, | 42 | first piston, |
| 43 | first flange, | 44 | second flange, |
| 45 | second connection head, | 45a | connection hole, |
| 46 | first connection head, | 47 | second piston, |
| 4a | sample accommodating cavity, | 4b | fluid medium cavity, |
| 4c | auxiliary hole, | 4d | fluid medium cavity, |
| 4e | passage, | 5 | synchronously rotating device, |
| 5a | multi-passage synchronous high pressure rotator, | | |
| 5b | cantilevered holder, | 5c | rotatable holder, |
| 5d | fixed holder, | 5b1 | transverse beam, |
| 5b2 | end plate, | 5b3 | third support plate, |
| 5b4 | guide rail, | 5b5 | slider, |
| 5b6 | lead screw, | 5b7 | nut seat, |
| 5b10 | upright plate, | 5b11 | bearing, |
| 5b12 | circular tube, | 5d1 | upright column, |
| 5d2 | bottom plate, | 5d3 | rib plate, |
| 5d4 | horizontal support plate, | 5d5 | rib plate, |
| 5d7 | motor, | 5c1 | central column, |
| 5c2 | second support plate, | 5c3 | rib plate, |
| 5c4 | gear, | 5c5 | bearing, |
| 5c6 | bearing, | 6 | control device, |
| 7 | automatic winder, | 7a | threaded rod, |
| 7b | nut, | 7c | sliding block, |
| 7d | bobbin, | 7e | bearing, |
| 7f | guide rod, | 7g | connecting plate, |
| 8 | stress-strain acquisition device, | 9 | test base, |
| 10 | control panel. | | |

DETAILED DESCRIPTION

An industrial Computed Tomography (CT) scanning test system is provided according to the present application, which can achieve real-time loading of a test sample and improve simulation accuracy of the system, and can achieve multi-directional loading on the sample, to meet test requirements.

For those skilled in the art to better understand technical solutions of the present application, the present application is described in detail in conjunction with drawings and embodiments hereinafter.

Reference is made to FIG. 1, which is a schematic view showing the structure of an industrial CT scanning test system according to an embodiment of the present application.

An industrial CT scanning test system is provided according to the present application. This system includes a test base 9, a multi-axis motion swivel table 2 supported on the test base 9, a ray generator 1, an image acquisition device 3, a fluid pressure loading device 4, and a control device 6. The multi-axis motion swivel table 2 is provided with a sample stage configured to allow a sample to be placed thereon. The sample stage may be rotated or moved in a predetermined direction with respect to the test base 9 according to test requirements. The predetermined direction here may be a direction along a principal ray beam, i.e., a front-and-rear direction, may also be a direction perpendicular to the principal ray beam in a horizontal plane, i.e., a right-and-left direction, and may also be a direction perpendicular to the principal ray beam in a vertical plane, i.e., an up-and-down direction. Similarly, the rotation of the sample stage may be a rotation about a vertical direction. Generally, in order to achieve the above functions of rotation and various directional linear movements, multiple sample stages may be provided, including a rotatable sample stage, a sample stage movable in the front-and-rear direction, a sample stage movable in the right-and-left direction and a sample stage movable in the up-and-down direction. Each of the sample stages may be driven to move by a motor. The motors are connected to the control device 6 via control lines (power supply lines and signal lines). An operator may control the motors by operating the control device 6, to allow sample stages to perform corresponding motions.

At present, rays emitted by the ray generator 1 are generally X-rays. Of course other types of rays may also be employed. Herein, the technical solution is introduced by taking X-rays as an example. The ray generator 1 may include a ray tube, a high pressure generator 1b and a control cabinet 2e. Since X-ray is radioactive, the ray generator 1 is generally placed inside a shield room. The ray tube is connected to the high pressure generator 1b and the control cabinet 2e via high voltage cables and control lines. The control cabinet 2e is connected to the control device 6 via a network cable. The control device 6 can adjust parameters for generating rays, such as the voltage and the current, and perform machine training and calibration. In consideration of safety of a tester, a beam emitting control switch of the X-ray control cabinet 2e is connected to a trigger of a lead door and an indicator lamp of the shield room, to ensure that the indicator lamp is on when rays are emitted and no rays will be emitted when the lead door is open.

The image acquisition device 3 is arranged at a side of the industrial CT scanning test system opposite to the ray generator 1 and is configured to acquire the rays emitted by the ray generator 1 and perform the imaging of the sample based on the acquired rays. The image acquisition device 3 may include a flat panel detector and a movable platform. The flat panel detector is fixed on the movable platform. The movable platform may move with respect to the test base 9 along an emitting direction of the principal ray beam, to achieve imaging at different magnifications. The movable platform may be driven to move by a motor, and of course may be driven to move by other components as well.

The movable platform may be made of aluminium alloy sections. The movable platform includes two upright columns, a transverse beam, a rib plate and etc., as long as the movable platform can provide a reliable support to the flat panel detector. The movement of the movable platform may be realized by the cooperation of a guide rail and a slider. The flat panel detector may be purchased according to required models, and parameters such as effective area, the number of picture elements, gray scale may be selected according to requirements.

It is to be noted that the ray detector in the image acquisition device 3 is not limited to the above flat panel detector, but may also be other types of detectors, as long as the above function can be achieved.

The fluid pressure loading device 4 is configured to perform real-time loading on the sample with loads in different directions according to test requirements. In a scanning experiment, the fluid pressure loading device 4 and the sample are placed together on the sample stage of the multi-axis motion swivel table 2. The fluid may be a liquid such as a hydraulic oil or water, and may also be a gas. The fluid pressure loading device 4 may include at least one loading cylinder, and the loading cylinder is used to load pressure on the sample.

The sample mentioned herein may be a geotechnical sample and may also be other types of samples. Herein, the geotechnical sample is taken as an example to be tested, to specifically illustrate the technical effects of the test system provided herein.

In the industrial CT scanning test system provided herein, the fluid pressure loading device 4 is employed, the self weight of the loading device is reduced as much as possible, and the loading device can provide a large loading force, and the requirements of deformation and destructive tests for most of geotechnical materials may be met. Also, the loading device of the test system and the sample are placed together on the sample stage of the multi-axis motion swivel table 2, and the loading force applied onto the geotechnical sample by the loading cylinder may be adjusted in real time according to test requirements, thus achieving the real-time adjustment of the loading force applied on the sample, and improving the efficiency of the test.

Also, the loading of forces in different directions on the sample may be realized by adjusting the number of loading cylinders. For example, providing two loading cylinders may realize the loading of forces in two directions on the sample. Providing three loading cylinders may realize the loading of forces in three different directions on the sample, for example, a simulation experiment in which forces in three-axis coordinate system are loaded may be performed.

Figure 2:
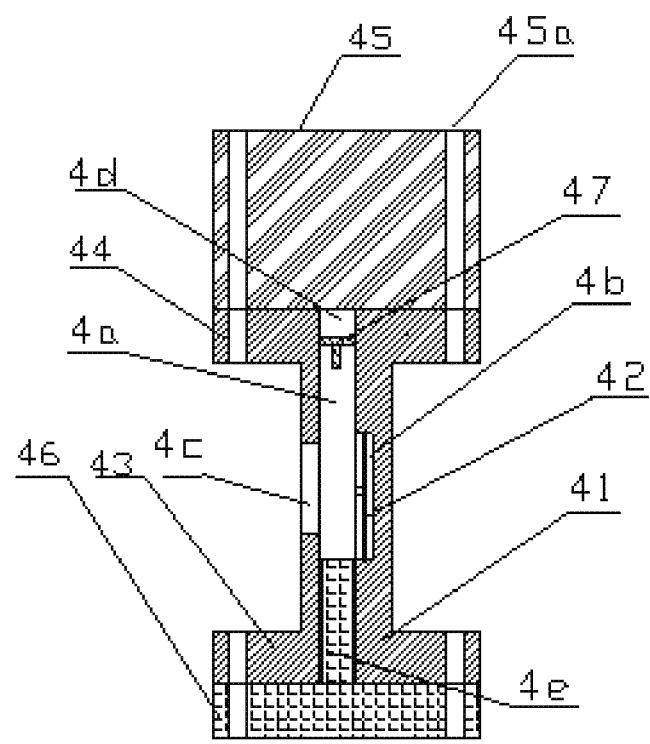
FIG. 2 is a schematic view showing the structure of a fluid pressure loading device according to a specific embodiment of the present application.
Figure 3:
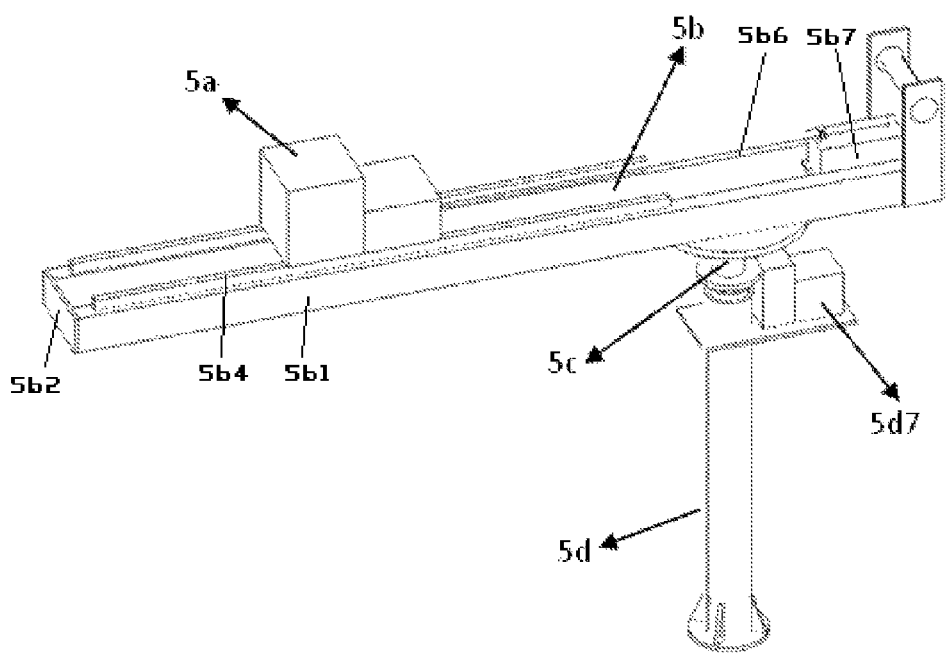
FIG. 3 is a schematic view showing the structure of a synchronously rotating device according to an embodiment of the present application.

Reference is also made to FIG. 2, which is a schematic view showing the structure of a fluid pressure loading device in a specific embodiment of the present application. Only two loading directions, including a vertical direction and a horizontal direction, are shown in FIG. 2.

In a specific embodiment, the fluid pressure loading device 4 includes a body 41. A sample accommodating cavity 4a and at least one fluid medium cavity are provided inside the body 41. The sample accommodating cavity 4a is configured to accommodate and fix the sample. A piston is provided in each of the fluid medium cavities, and the piston separates the respective fluid medium cavity into two chambers, in which, one chamber is in communication with an external hydraulic medium via an oil passage provided inside the body 41, and the other chamber is in communication with the sample accommodating cavity 4a. One end, facing the sample accommodating cavity 4a, of each piston may extend into the sample accommodating cavity 4a. The fluid medium cavity and the piston constitute a loading cylinder.

In this embodiment, to perform a force loading on a sample, firstly the sample is placed inside the body 41 of the loading device, and then an external medium source is activated to fill a fluid medium into a fluid medium cavity inside the body 41. Under the pushing action of the fluid medium flowing into the fluid medium cavity, the piston placed inside the fluid medium cavity is moved toward the sample accommodating cavity 4a, and as the fluid medium is continuously filled, the piston abuts against the sample and applies a force onto the sample. An operator may calculate the force applied onto the sample based on the pressure of the fluid medium in a pipeline and the area of the piston, thereby realizing the force loading on the sample.

This manner of force loading on the sample can provide pressures in different directions by using the embedded loading cylinders, and the pressure may reach 200 MPa by taking a liquid medium as an example, and this manner may be used to achieve three-axial, two-axial and single-axial loading tests. The structure of the loading device is simple and the volume thereof may be designed to match with the sample.

The body 41 may be made of an aluminium alloy material with high strength and light weight, which may meet the strength requirement for the body 41 in the case of being loaded with a large load, and the requirement that the ray can penetrate the body 41 when CT scan is performed. Also, the self-weight of the body is reduced, which may meet the restriction requirement of the swivel table for the weight of a piece to be scanned.

In the case that the forces applied onto the sample are two-dimensional forces in two mutually perpendicular directions (two-axial forces), correspondingly, the number of the fluid medium cavities is two, including a first fluid medium cavity 4b and a second fluid medium cavity 4d, and correspondingly, the pistons include a first piston 42 and a second piston 47. The first piston 42 is placed inside the first fluid medium cavity 4b, the second piston 47 is placed inside the second fluid medium cavity 4d, and also, an axial direction of the first piston 42 and an axial direction of the second piston 47 are arranged to be perpendicular to each other. Herein, the axial direction of the first piston 42 is in the horizontal direction and the axial direction of the second piston 47 is in the vertical direction. Of course, the axial directions of the first piston 42 and the second piston 47 may be set according to requirements of practical loading forces.

To simulate three-axis forces, the fluid medium cavities further include a third fluid medium cavity, and a third piston is provided inside the third fluid medium cavity. An axial direction of the third piston, the axial direction of the second piston and the axial direction of the first piston constitute a three-axis coordinate system. Although a schematic view of the third fluid medium cavity is not shown herein, those skilled in the art may easily understand and implement this technical solution based on the description herein.

Further, in order to obtain a large loading force for a sample with a small internal pressure in a loading cylinder, the piston may be designed to have a variable cross section, for example, the cross sectional dimension of a first end surface of the piston is greater than the cross sectional dimension of a second end surface of the piston. The first end surface is an end surface towards the end of the fluid medium cavity, and the second end surface is an end surface towards the end of the sample accommodating cavity 4a.

In a practical test, the working pressure inside the loading cylinder is relatively small, and it is easy to realize oil pipe connection and meet the pressure for the pump, however, the pressure loaded on the sample is large, thus facilitating achieving a large loading force, and especially for a direction Z (the vertical direction), this part of the body 41 in the direction Z does not interfere with the penetrating of the rays, and thus has no special requirement on the dimension in the direction Z.

In addition, for the loading in two directions X, Y, on the premise that the magnitude of the loading forces are ensured, the effects caused by the rays on the sample when the rays penetrate the sample should be reduced as much as possible. Therefore, the body 41 is required to have a sufficiently small profile dimension, and its experimental load must be ensured, hence, in manufacturing, the body 41 is processed to apply loads in an asymmetric manner, that is, in a longitudinal cross section of the body 41, a wall thickness, at a side where the fluid medium cavity is provided, of the body 41 is greater than a wall thickness, at the opposite side, of the body 41. As also illustrated in FIG. 2, a thickness, at a side where the first fluid medium cavity 4b is provided, of the body 41 is greater than the thickness, at the opposite side, of the body 41.

Also, the body 41 is further provided with an auxiliary hole 4c at a part opposite to the fluid medium cavity, and the auxiliary hole 4c has a radial dimension smaller than the radial dimension of the fluid medium cavity, and the auxiliary hole 4c may reduce difficulty in processing the fluid medium cavity. Of course, in the case that a force loading experiment is performed, the auxiliary hole 4c needs to be blocked by a plug.

In addition, for ensuring the processing accuracy of an inner wall of the fluid medium cavity, and for preventing the loading oil passage from interfering with the rays, oil ports configured to communicate with the external liquid medium are all arranged in an upper end surface of the body 41, and the oil ports are in communication with the fluid medium cavities via inner passages respectively. The oil passages are directly processed in the body 41, thereby avoiding the interference to the rays caused by external oil pipes.

For facilitating arranging the sample inside the sample accommodating cavity 4a from the outside, the body 41 is further provided with a passage 4e configured to communicate a lower surface of the body 41 with the sample accommodating cavity 4a, thus the sample can be easily disposed into the sample accommodating cavity 4a from the passage 4e. An inlet end of the passage 4e is provided with a plug.

For facilitating mounting and assembling the body 41, an upper end and a lower end of the body 41 may further be provided with flanges, and connection heads are connected to the flanges at two ends of the body 41 via bolts. At the lower end of the body 41, a first flange 43 and a first connection head 46 are cooperatively connected, and at the upper end of the body 41, the second flange 44 and the second connection head 45 are cooperatively connected. The connection heads and the flanges may be provided with connection holes, and the bolts pass through the connection holes of the connection heads and the flanges, to be fixed to corresponding nuts respectively, thereby achieving the connection between the connection heads and the flanges. FIG. 2 shows a connection hole 45a in the second connection head 45.

In addition, for ensuring the sealing between the piston and the fluid medium cavity, a sealing component may be further provided between the piston and the fluid medium cavity. The sealing component may be a sealing ring, a mounting groove is processed in a circumferential wall of the piston, and the sealing ring is disposed inside the mounting groove.

The sample stage according to the above embodiments is movable or rotatable with respect to the test base 9, that is, the body 41 according to the above embodiments also moves with respect to the test base 9 during the test. Therefore, for avoiding the interference of the pipeline, configured to communicate with the body 41, of an external oil passage, the following arrangement may be further made.

Figure 4:
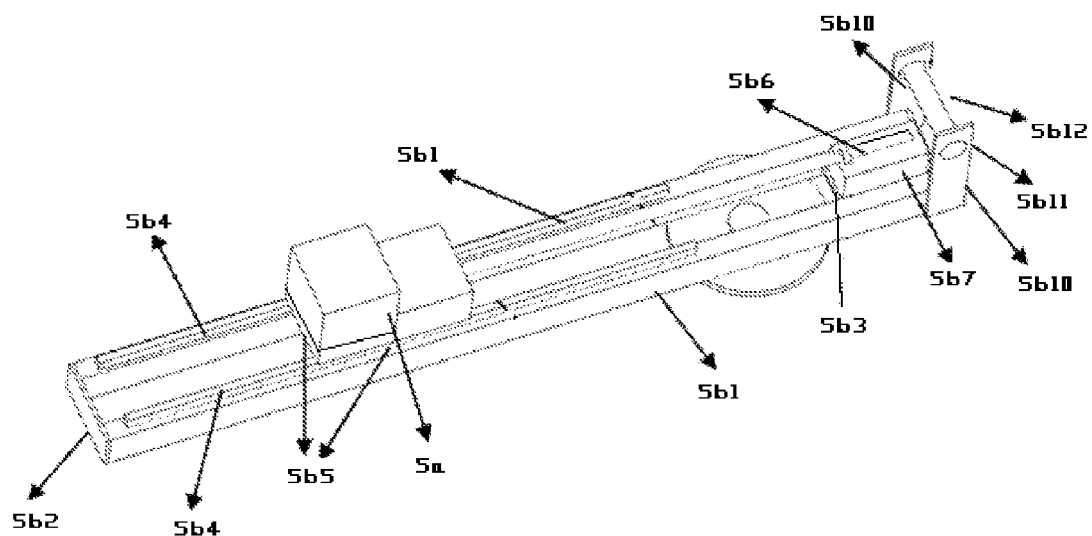
FIG. 4 is a schematic view showing the structure of a cantilevered holder.
Figure 5:
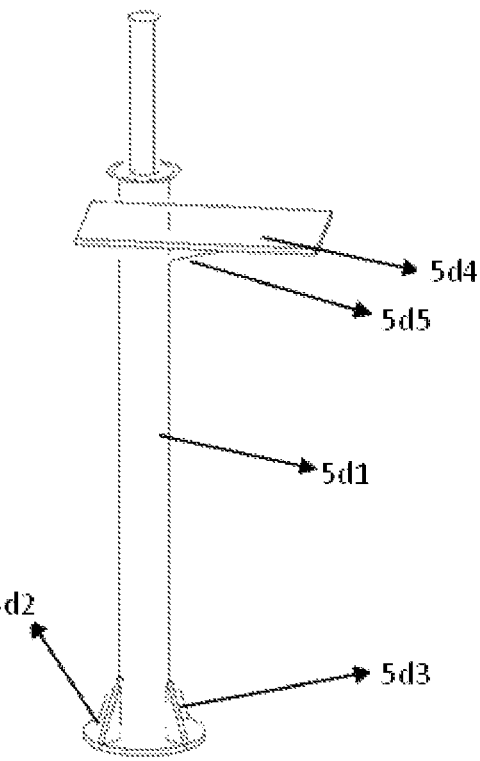
FIG. 5 is a schematic view showing the structure of a fixed holder.
Figure 6:
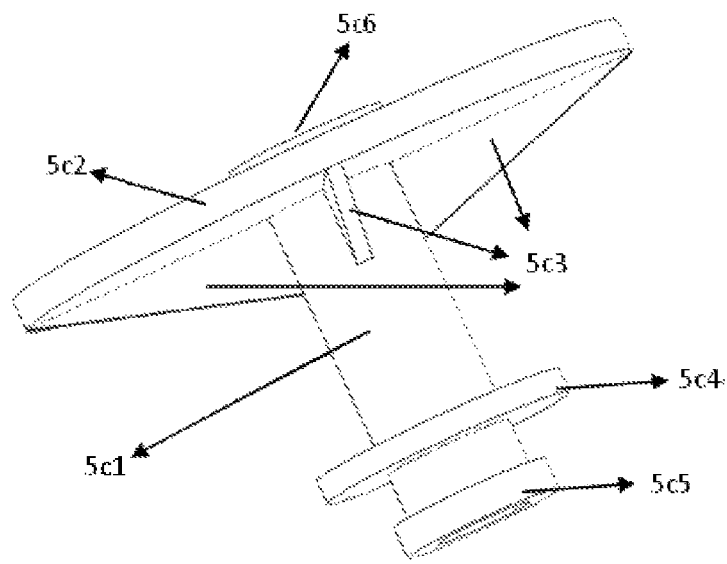
FIG. 6 is a schematic view showing the structure of a rotatable holder.

Reference is made to FIGS. 3 to 6, FIG. 3 is a schematic view showing the structure of a synchronously rotating device according to an embodiment of the present application; FIG. 4 is a schematic view showing the structure of a cantilevered holder; FIG. 5 is a schematic view showing the structure of a fixed holder, and FIG. 6 is a schematic view showing the structure of a rotatable holder.

The industrial CT scanning test system according to the above embodiments may be further provided with a synchronously rotating device 5. The synchronously rotating device 5 includes a fixed holder 5d and a cantilevered holder 5b. The cantilevered holder 5b is disposed above the loading cylinder, the fixed holder 5d has a lower end supported on the test base 9, and an upper end vertically rotatably connected to the cantilevered holder 5b, that is, the cantilevered holder 5b is able to rotate around the vertical direction with respect to the fixed holder 5d.

A guide rail 5b4, a slider 5b5 configured to cooperate with the guide rail 5b4, and a driving component configured to drive the slider 5b5 to move along the guide rail 5b4 are arranged on the cantilevered holder 5b. A medium pipeline configured to communicate with the loading cylinder is positioned on the slider 5b5, to allow the medium pipeline to slide with respect to the guide rail 5b4 along with the slider 5*b*5, and the medium pipeline extends downward from the slider 5*b*5 to connect the loading cylinder on the sample stage. The control device 6 may control the driving component to act, to allow the slider 5*b*5 to be always located right above the loading cylinder, that is, the slider 5*b*5 may act synchronously with the loading cylinder. In this way, the position of the slider 5*b*5 may be adjusted in real time according to different sizes of samples and different positions of the sample stage in cases of different magnifications, to allow the medium pipeline to be always perpendicular to the loading cylinder, avoid the pipeline from being wound on the loading cylinder, and ensure the normal action of the loading cylinder.

The synchronously rotating device 5 may further include a multi-passage high pressure rotator 5*a* fixedly connected to the slider 5*b*5. The multi-passage high pressure rotator 5*a* includes a fixed-end pipe joint and a rotary-end pipe joint which are in communication with each other via an internal passage. The fixed-end pipe joint is in communication with a driving source via an oil pipe, and the rotary-end pipe joint is in communication with the loading cylinder. The rotary-end pipe joint is rotatable synchronously along with the rotation of the sample stage and will not interfere with the rotation of the loading cylinder.

In the above various embodiments, the driving component in the synchronously rotating device 5 may include a motor, a lead screw 5*b*6, and a nut seat 5*b*7 configured to cooperate with a threaded end of the lead screw 5*b*6. The threaded end of the lead screw 5*b*6 is arranged in an inner threaded hole of the nut seat 5*b*7, and another end of the lead screw 5*b*6 is fixedly connected to the slider 5*b*5. The motor drives the lead screw 5*b*6 to rotate, thereby allowing the lead screw 5*b*6 to drive the slider 5*b*5 to reciprocate.

The synchronously rotating device 5 in the above embodiments may further include a rotatable holder 5*c* arranged between the fixed holder 5*d* and the cantilevered holder 5*b*. The fixed holder 5*d* includes an upright column 5*d*1, and the bottom of the upright column 5*d*1 is supported on the test base 9, and an upper end of the upright column 5*d*1 is further provided with a horizontal support plate 5*d*4. For increasing the reliability of the connection, a rib plate 5*d*5 may be further provided between the horizontal support plate 5*d*4 and the upright column 5*d*1, and a lower end of the upright column 5*d*1 may be further provided with a bottom plate 5*d*2, and a rib plate 5*d*3 is further provided between the bottom plate 5*d*2 and the upright column 5*d*1.

The rotatable holder 5*c* includes a central column 5*c*1, and a lower end of the central column 5*c*1 is inserted into the upper end of the upright column 5*d*1 and is circumferentially rotatably connected to the upper end of the upright column 5*d*1 via a bearing 5*c*5. A gear 5*c*4 is further fixed on the central column 5*c*1, and a motor 5*d*7 configured to drive the gear 5*c*4 to rotate is further provided, and is fixed on the horizontal support plate 5*d*4. The motor 5*d*7 drives, by the gear 5*c*4, the central column 5*c*1 to rotate with respect to the upright column 5*d*1. A second support plate 5*c*2 is fixed to an upper end of the central column 5*c*1, and the cantilevered holder 5*b* is fixed to the second support plate 5*c*2.

For ensuring the reliability of the fixing connection between the second support plate 5*c*2 and the central column 5*c*1, a rib plate 5*c*3 may be further provided between the central column 5*c*1 and the second support plate 5*c*2, and also, for increasing the flexibility of the rotation of the central column 5*c*1, the upper end of the central column 5*c*1 may also be provided with a positioning bearing 5*c*6.

The cantilevered holder 5*b* includes two transverse beams 5*b*1 extending horizontally, an end plate 5*b*2 connected to front ends of the two transverse beams 5*b*1, and a third support plate 5*b*3 connected to rear ends of the two transverse beams 5*b*1. The driving component is arranged above the third support plate 5*b*3, and the third support plate 5*b*3 is rotatably connected to the fixed holder 5*d*, and the guide rail 5*b*4 is arranged on upper surfaces of the two transverse beams 5*b*1.

The rear ends of the transverse beams 5*b*1 are further provided with two parallel upright plates 5*b*10, and a circular tube 5*b*12 is further connected between the two parallel upright plates 5*b*10. The circular tube 5*b*12 is rotatably connected to the two parallel upright plates 5*b*10 via bearings 5*b*11. The pipeline is rested on the surface of the circular tube 5*b*12, and as the slider 5*b*5 slides forward and backward, the pipeline may roll along with the circular tube 5*b*12, to reduce the friction between the pipeline and the circular tube 5*b*12.

For accurately obtaining loading forces applied on the sample by the loading cylinders, a stress-strain acquisition device 8 may be further provided on the test base 9, to acquire stress-strain parameters of the sample in various directions. The control device 6 controls the pressure of the fluid medium in the fluid pressure loading device 4 according to the stress-strain parameters. The stress-strain acquisition device 8 includes a sensor and a signal acquisition apparatus. The sensor is arranged on the body, the signal acquisition apparatus is generally arranged on the test base 9 right below the sample stage, and the signal acquisition apparatus and the sensor are connected by signal lines and the like. For avoiding the winding of the signal lines when the sample stage rotates, further arrangements are made herein, and are described as follow.

Figure 7:
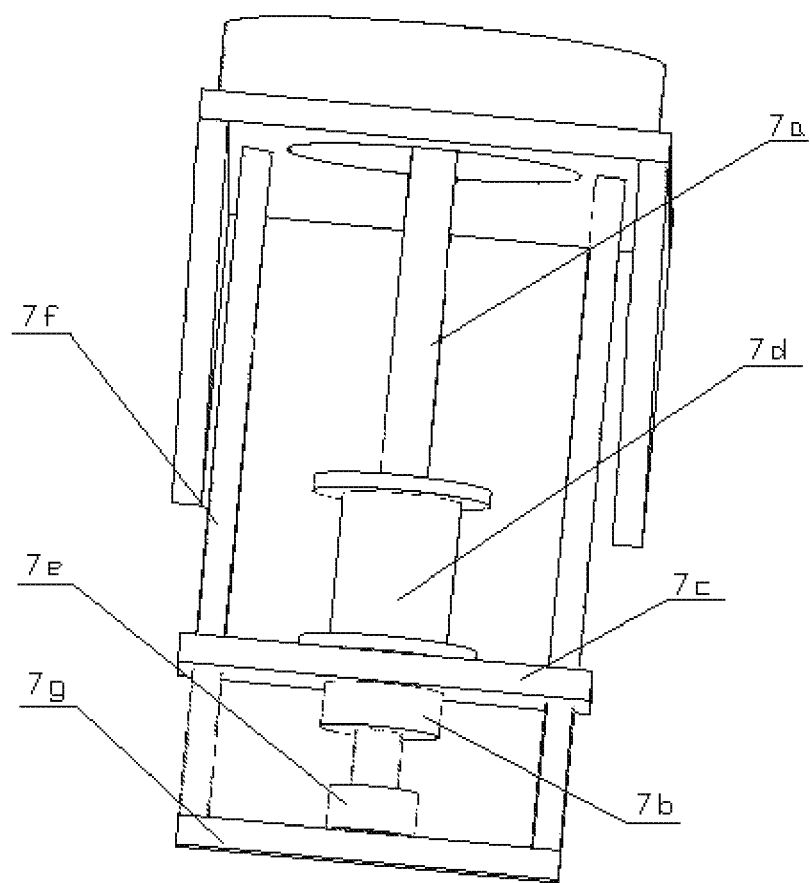
FIG. 7 is a schematic view showing the structure of an automatic winder according to an embodiment of the present application.
Figure 8:
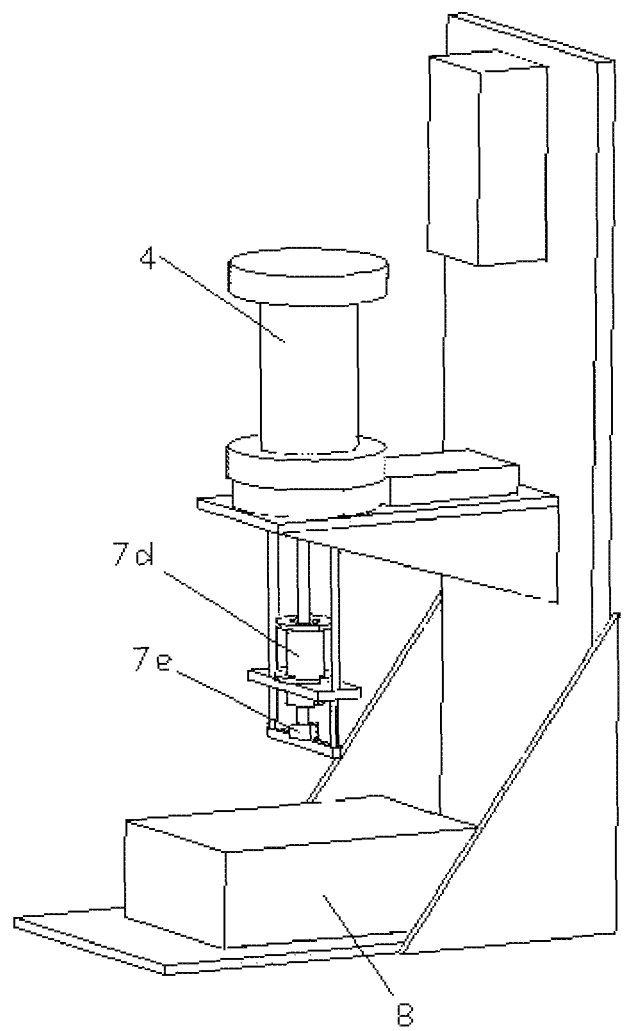
FIG. 8 is a schematic view showing the assembly of the automatic winder and a sample stage.

Reference is made to FIGS. 7 and 8, FIG. 7 is a schematic view showing the structure of an automatic winder according to an embodiment of the present application; and FIG. 8 is a schematic view showing the assembly of the automatic winder and the sample stage.

The industrial CT scanning apparatus in the above embodiments may further include an automatic winder 7 arranged below the sample stage. The automatic winder 7 includes a threaded rod 7*a*, a nut assembly and a bobbin 7*d*. An upper end of the threaded rod 7*a* is fixedly connected to the sample stage, and a lower end of the threaded rod 7*a* passes through a threading hole of the multi-axis motion swivel table 2 to extend downwards. The nut assembly includes a nut 7*b* and a limiting component configured to limit the position of the nut 7*b* with respect to a fixing frame of the multi-axis motion swivel table 2 circumferentially. The nut 7*b* is arranged on an outer threaded portion of the threaded rod 7*a*, and the bobbin 7*d* is sleeved on the threaded rod 7*a*, and the bobbin 7*d* is axially movably connected to the threaded rod 7*a*, and the bobbin 7*d* is fixedly connected to the nut 7*b*.

Firstly, in mounting process, the signal line in the loading device on the sample stage is wound around the surface of the bobbin 7*d*, to allow the signal line to be transferred to other connection components after the signal line is wound on the surface of the bobbin 7*d*. In this way, when the sample stage rotates, the threaded rod 7*a* also rotates synchronously with the sample stage, and since the nut 7*b* is fixed circumferentially, the nut 7*b* moves upward or downward with respect to the threaded rod 7*a*, and thus the bobbin 7*d* fixed to the nut 7*b* also moves upward or downward along with the nut 7*b*. In this way, the signal line transferred from an edge through hole of the rotatable sample stage also rotates along with the swivel table, and therefore the signal line rotates about the bobbin 7*d*. The signal line rotates and moves upward and downward with respect to the bobbin 7d at the same time, to form a spiral movement, thereby automatically winding the signal line on the surface of the bobbin 7d, and preventing the signal line from being knotted to interfere with the rotation of the loading device when the sample stage rotates.

In a specific embodiment, the limiting component may include guide rods 7f respectively located at two sides of the threaded rod 7a, and a sliding plate 7c sleeved on the two guide rods 7f and slidably connected to the guide rods 7f, and the nut 7b is fixed to the sliding plate 7c. The structure is simple, and facilitates the arrangement of the nut 7b.

Further, tail ends of the two guide rods 7f are further connected with a connecting plate 7g, a bearing 7e is provided on the connecting plate 7g, and a free end of the threaded rod 7a is connected to the connecting plate 7g via the bearing 7e. In this structure, the position of the free end of the threaded rod 7a is also relatively limited, which facilitates ensuring the stability of the rotation of the threaded rod 7a.

Of course, a control panel 10 may be further provided in the shield room. With the control panel 10, the parameters of the loading device may be set and the loaded loads on the sample may be displayed by a touch screen interface of the control panel 10, to perform loading on the sample. The specific structure of the control panel 10 may refer to the structure of a conventional apparatus, which will not be described here in detail.

It is to be noted that, terms indicating directions and positions herein, such as "upper", "lower", are defined by taking the positional relationship between the various components in FIGS. 1 to 8 as a reference, and are only for clarity of description of the technical solutions, and does not limit the scope of the present application.

The industrial CT scanning test system according to the present application is described in detail hereinbefore. The principle and the embodiments of the present application are illustrated herein by specific examples. The above description of the examples is only intended to help the understanding of the method and idea of the present application. It should be noted that, for the person skilled in the art, a few of modifications and improvements may be made to the present application without departing from the principle of the present application, and these modifications and improvements are also deemed to fall into the scope of the present application defined by the claims.

What is claimed is:

1. An industrial CT scanning test system, comprising a test base, a multi-axis motion swivel table supported on the test base, a ray generator, an image acquisition device, and a fluid pressure loading device, and further comprising a control device; wherein,
the multi-axis motion swivel table is provided with a sample stage configured to allow a sample to be placed thereon, and the sample stage is rotatable or movable in a preset direction with respect to the test base according to test requirements;
the ray generator is configured to emit rays required for scanning the sample;
the image acquisition device is arranged in a side opposite to the ray generator, and is configured to acquire the rays emitted by the ray generator and perform imaging of the sample according to the rays acquired;
the fluid pressure loading device comprises at least one loading cylinder, and in case of performing a scanning experiment, the at least one loading cylinder is placed on the sample stage of the multi-axis motion swivel table together with the sample, and real-time loading of loads in different directions on the sample is performed according to test requirements; the fluid pressure loading device comprises a body, and a sample accommodating cavity and at least one fluid medium cavity are provided inside the body, a piston is provided in each of the at least one fluid medium cavity and separates the respective fluid medium cavity into two chambers, comprising one chamber in communication with an external hydraulic medium via an oil passage provided inside the body, and another chamber in communication with the sample accommodating cavity; and one end, facing the sample accommodating cavity, of each piston is extendable into the sample accommodating cavity; and the fluid medium cavity and the piston constitute the loading cylinder; and
the control device is configured to control actions of the multi-axis motion swivel table, the ray generator, the image acquisition device, and the fluid pressure loading device; and
the industrial CT scanning test system further comprises a synchronously rotating device, wherein the synchronously rotating device comprises a fixed holder and a cantilevered holder, a lower end of the fixed holder is supported on the test base, and an upper end of the fixed holder is vertically rotatably connected to the cantilevered holder;
a guide rail, a slider configured to cooperate with the guide rail to slide, and a driving component configured to drive the slider to move along the guide rail are provided on the cantilevered holder; and
a medium pipeline configured to communicate with the loading cylinder is limited in the slider, and extends downward from the slider to connect the loading cylinder located on the sample stage.

2. The industrial CT scanning test system according to claim 1, wherein the fluid medium cavities comprises a first fluid medium cavity and a second fluid medium cavity, correspondingly, the pistons comprises a first piston and a second piston, the first piston is placed inside the first fluid medium cavity, the second piston is placed inside the second fluid medium cavity, and an axial direction of the first piston and an axial direction of the second piston are arranged to be perpendicular to each other.

3. The industrial CT scanning test system according to claim 2, wherein the fluid medium cavities further comprise a third fluid medium cavity, a third piston is provided inside the third fluid medium cavity, and an axial direction of the third piston, the axial direction of the second piston and the axial direction of the first piston constitute a three-axis coordinate system, and one of the fluid medium cavities is vertically arranged.

4. The industrial CT scanning test system according to claim 1, wherein in an axial direction of the piston, a cross sectional dimension of a first end surface of the piston is greater than a cross sectional dimension of a second end surface of the piston, the first end surface is an end surface towards an end of the fluid medium cavity, and the second end surface is an end surface towards an end of the sample accommodating cavity.

5. The industrial CT scanning test system according to claim 1, wherein the body is further provided with an auxiliary hole at a portion opposite to the fluid medium cavity, and the auxiliary hole has a radial dimension smaller than a radial dimension of the fluid medium cavity; and a plug matching with the auxiliary hole is further provided.

6. The industrial CT scanning test system according to claim 1, wherein the body is further provided with a passage configured to communicate a lower surface of the body with the sample accommodating cavity, to facilitate disposing the sample into the sample accommodating cavity through the passage, and an inlet end of the passage is provided with a plug.

7. The industrial CT scanning test system according to claim 1, wherein oil ports configured to communicate with an external fluid medium source are all arranged in an upper end surface of the body, and the oil ports are in communication with respective fluid medium cavities via internal oil passages; and
the industrial CT scanning test system further comprises two connection heads, wherein an upper end and a lower end of the body are each provided with a flange, and the two connection heads are connected to the flanges at the two ends of the body via bolts.

8. The industrial CT scanning test system according to claim 1, wherein the cantilevered holder comprises two transverse beams extending horizontally, an end plate connected to front ends of the two transverse beams, and a third support plate connected to rear ends of the two transverse beams, the driving component is arranged above the third support plate, and the third support plate is rotatably connected to the fixed holder, and the guide rail is arranged on upper surfaces of the two transverse beams.

9. The industrial CT scanning test system according to claim 1, wherein the synchronously rotating device further comprises a multi-passage high pressure rotator fixedly connected to the slider, the multi-passage high pressure rotator comprises a fixed-end pipe joint and a rotary-end pipe joint which are in communication with each other via an internal passage, and the fixed-end pipe joint is in communication with a driving source via a pipeline, and the rotary-end pipe joint is in communication with the loading cylinder via a pipeline, and the rotary-end pipe joint is rotatable synchronously with the sample stage.

10. The industrial CT scanning test system according to claim 1, further comprising a rotatable holder arranged between the fixed holder and the cantilevered holder, wherein,
the fixed holder comprises an upright column, and a bottom of the upright column is supported on the test base, and an upper end of the upright column is further provided with a horizontal support plate; and
the rotatable holder comprises a central column, a lower end of the central column is inserted into the upper end of the upright column and is circumferentially rotatably connected to the upper end of the upright column via a bearing, a gear is further fixed onto the central column, and a motor configured to drive the gear to rotate is further provided, and is fixed to the horizontal support plate; and a second supporting plate is fixed to an upper end of the central column, and the cantilevered holder is fixed to the second support plate.

11. The industrial CT scanning test system according to claim 1, wherein the driving component comprises a motor, a lead screw, and a nut seat configured to cooperate with a threaded end of the lead screw, the threaded end of the lead screw is arranged in an inner threaded hole of the nut seat, and another end of the lead screw is fixedly connected to the slider, and the motor is configured to drive the lead screw to rotate, to allow the lead screw to drive the slider to reciprocate.

12. The industrial CT scanning test system according to claim 1, further comprising an automatic winder arranged below the sample stage, wherein the automatic winder comprises a threaded rod, a nut assembly and a bobbin, an upper end of the threaded rod is fixedly connected to the sample stage, and a lower end of the threaded rod passes through a threading hole of the sample stage to extend downward;
the nut assembly comprises a nut and a limiting component configured to limit the position of the nut with respect to a fixing frame of the multi-axis motion swivel table circumferentially, and the nut has inner screw threads configured to cooperate with an outer threaded portion of the threaded rod; and the bobbin is sleeved on the threaded rod, the bobbin and the threaded rod are axially movably connected, and the bobbin is fixedly connected to the nut; and
the limiting component comprises guide rods respectively located at two sides of the threaded rod and a sliding plate sleeved on the two guide rods, the sliding plate is axially slidably connected to the guide rods, and the sliding plate is fixedly connected to the nut.

13. The industrial CT scanning test system according to claim 12, wherein the limiting component further comprises a connecting plate fixedly connected to tail ends of the two guide rods, a bearing is provided on the connecting plate, and a free end of the threaded rod is connected to the connecting plate via the bearing.

14. The industrial CT scanning test system according to claim 1, wherein the image acquisition device comprises a flat panel detector and a movable platform, and the flat panel detector is supported on the movable platform, and the movable platform is movable with respect to the test base in an emitting direction of a principle ray beam.

15. The industrial CT scanning test system according to claim 1, further comprising a stress-strain acquisition device configured to acquire stress-strain parameters of the sample in various directions; wherein the control device is configured to control a pressure of a fluid medium in the fluid pressure loading device according to the stress-strain parameters.

16. The industrial CT scanning test system according to claim 2, further comprising an automatic winder arranged below the sample stage, wherein the automatic winder comprises a threaded rod, a nut assembly and a bobbin, an upper end of the threaded rod is fixedly connected to the sample stage, and a lower end of the threaded rod passes through a threading hole of the sample stage to extend downward;
the nut assembly comprises a nut and a limiting component configured to limit the position of the nut with respect to a fixing frame of the multi-axis motion swivel table circumferentially, and the nut has inner screw threads configured to cooperate with an outer threaded portion of the threaded rod; and the bobbin is sleeved on the threaded rod, the bobbin and the threaded rod are axially movably connected, and the bobbin is fixedly connected to the nut; and
the limiting component comprises guide rods respectively located at two sides of the threaded rod and a sliding plate sleeved on the two guide rods, the sliding plate is axially slidably connected to the guide rods, and the sliding plate is fixedly connected to the nut.

17. The industrial CT scanning test system according to claim 3, further comprising an automatic winder arranged below the sample stage, wherein the automatic winder comprises a threaded rod, a nut assembly and a bobbin, an upper end of the threaded rod is fixedly connected to the sample stage, and a lower end of the threaded rod passes through a threading hole of the sample stage to extend downward;

the nut assembly comprises a nut and a limiting component configured to limit the position of the nut with respect to a fixing frame of the multi-axis motion swivel table circumferentially, and the nut has inner screw threads configured to cooperate with an outer threaded portion of the threaded rod; and the bobbin is sleeved on the threaded rod, the bobbin and the threaded rod are axially movably connected, and the bobbin is fixedly connected to the nut; and the limiting component comprises guide rods respectively located at two sides of the threaded rod and a sliding plate sleeved on the two guide rods, the sliding plate is axially slidably connected to the guide rods, and the sliding plate is fixedly connected to the nut.

18. The industrial CT scanning test system according to claim 4, further comprising an automatic winder arranged below the sample stage, wherein the automatic winder comprises a threaded rod, a nut assembly and a bobbin, an upper end of the threaded rod is fixedly connected to the sample stage, and a lower end of the threaded rod passes through a threading hole of the sample stage to extend downward;

the nut assembly comprises a nut and a limiting component configured to limit the position of the nut with respect to a fixing frame of the multi-axis motion swivel table circumferentially, and the nut has inner screw threads configured to cooperate with an outer threaded portion of the threaded rod; and the bobbin is sleeved on the threaded rod, the bobbin and the threaded rod are axially movably connected, and the bobbin is fixedly connected to the nut; and the limiting component comprises guide rods respectively located at two sides of the threaded rod and a sliding plate sleeved on the two guide rods, the sliding plate is axially slidably connected to the guide rods, and the sliding plate is fixedly connected to the nut.

19. The industrial CT scanning test system according to claim 5, further comprising an automatic winder arranged below the sample stage, wherein the automatic winder comprises a threaded rod, a nut assembly and a bobbin, an upper end of the threaded rod is fixedly connected to the sample stage, and a lower end of the threaded rod passes through a threading hole of the sample stage to extend downward;

the nut assembly comprises a nut and a limiting component configured to limit the position of the nut with respect to a fixing frame of the multi-axis motion swivel table circumferentially, and the nut has inner screw threads configured to cooperate with an outer threaded portion of the threaded rod; and the bobbin is sleeved on the threaded rod, the bobbin and the threaded rod are axially movably connected, and the bobbin is fixedly connected to the nut; and the limiting component comprises guide rods respectively located at two sides of the threaded rod and a sliding plate sleeved on the two guide rods, the sliding plate is axially slidably connected to the guide rods, and the sliding plate is fixedly connected to the nut.

20. The industrial CT scanning test system according to claim 6, further comprising an automatic winder arranged below the sample stage, wherein the automatic winder comprises a threaded rod, a nut assembly and a bobbin, an upper end of the threaded rod is fixedly connected to the sample stage, and a lower end of the threaded rod passes through a threading hole of the sample stage to extend downward;

the nut assembly comprises a nut and a limiting component configured to limit the position of the nut with respect to a fixing frame of the multi-axis motion swivel table circumferentially, and the nut has inner screw threads configured to cooperate with an outer threaded portion of the threaded rod; and the bobbin is sleeved on the threaded rod, the bobbin and the threaded rod are axially movably connected, and the bobbin is fixedly connected to the nut; and the limiting component comprises guide rods respectively located at two sides of the threaded rod and a sliding plate sleeved on the two guide rods, the sliding plate is axially slidably connected to the guide rods, and the sliding plate is fixedly connected to the nut.

\* \* \* \* \*